United States Patent [19]

Kuroda et al.

[11] Patent Number: 4,956,250
[45] Date of Patent: Sep. 11, 1990

[54] AZULENIUM PHOTOCONDUCTOR FOR ELECTROPHOTOGRAPHY

[75] Inventors: Masami Kuroda; Yoshinobu Sugata; Noboru Furusho, all of Kawasaki, Japan

[73] Assignee: Fuji Electric Co., Ltd., Kanagawa, Japan

[21] Appl. No.: 326,800

[22] Filed: Mar. 21, 1989

[30] Foreign Application Priority Data

Mar. 23, 1988 [JP] Japan .................................. 63-68907
Aug. 23, 1988 [JP] Japan ................................. 63-209116

[51] Int. Cl.$^5$ ........................... G03G 5/06; G03G 5/14
[52] U.S. Cl. ........................................ 430/58; 430/75; 430/76
[58] Field of Search ........................ 430/58, 59, 75, 76

[56] References Cited

U.S. PATENT DOCUMENTS

| | | | |
|---|---|---|---|
| 3,484,237 | 12/1969 | Shattuck et al. | 430/81 |
| 4,150,987 | 1/1979 | Anderson et al. | 430/59 |
| 4,278,747 | 7/1981 | Murayama et al. | 430/82 |
| 4,353,971 | 3/1982 | Chang et al. | 430/58 |
| 4,367,273 | 1/1983 | Murayama et al. | 430/56 |
| 4,385,106 | 7/1983 | Sakai | 430/59 |
| 4,448,868 | 11/1984 | Suzuki et al. | 430/58 |
| 4,565,761 | 1/1986 | Katagiri et al. | 430/75 X |
| 4,629,670 | 12/1986 | Katagiri et al. | 430/72 X |
| 4,673,630 | 6/1987 | Katagiri et al. | 430/72 |
| 4,677,045 | 2/1987 | Champ et al. | 430/76 |
| 4,839,252 | 10/1989 | Murata et al. | 430/59 |
| 4,861,691 | 3/1989 | Kuroda et al. | 430/59 |
| 4,861,692 | 11/1989 | Kuroda et al. | 430/59 |

*Primary Examiner*—Roland E. Martin
*Attorney, Agent, or Firm*—Spencer & Frank

[57] ABSTRACT

A photoconductor for electrophotography comprises a novel azulenium compound as a charge generating substance. An azulenium compound is represented by the following general formula:

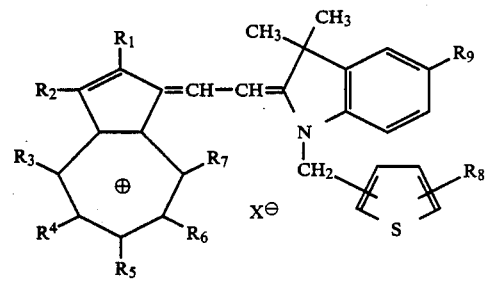

Wherein, each of $R_1$ to $R_9$ stands for a hydrogen atom, a halogen atom, an alkoxy group, or an alkyl group, an aryl group, both of which may have a substituent(s), and $X^{\ominus}$ stands for an anion residual group.

9 Claims, 1 Drawing Sheet

AZULENIUM PHOTOCONDUCTOR FOR ELECTROPHOTOGRAPHY

BACKGROUND OF THE INVENTION

1. Field of the Invention

The present invention relates to photoconductors for electrophotography, and particularly to a photoconductor for electrophotography which contains an azulenium compound in the photosensitive layer thereof formed on an electroconductive substrate.

2. Description of the Prior Art

Photosensitive materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and disazo compounds, and dispersions of such organic polymeric photoconductive substances in resin binder and films of organic photoconductive substance as mentioned above, deposited by means of vacuum evaporation.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the electric charge transportation upon receiving light. In an electrophotographic method using a photoconductor of the kind as mentioned above, for example, the Carlson's system is applied to image formation. The image formation according to this system comprises steps of subjecting a photoconductor in the dark to corona discharge to charge the photoconductor, exposing the surface of the charged photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralization of the residual charge with light (erasion), and so on to be ready for reuse.

Photoconductors for electrophotography in which use is made of organic materials have recently been put into practical use by virtue of the advantageous features of flexibility, thermal stability, and/or a film forming capacity. They include a photoconductor comprising poly-N-vinylcarbazole and 2,4,7-trinitrofluoren-9-on (disclosed in U.S. Pat. No. 3,484,237), a photoconductor using an organic pigment as a main component (disclosed in Japanese Patent Laid-Open No. 37,543/1972), and a photoconductor using as a main component a eutectic complex composed of a dye and resin (disclosed in Japanese Patent Laid-Open No. 10,785/1972). A number of novel hydrazone compounds and disazo compounds and the like have also been put into practical use for photoconductors.

Although organic materials have many advantageous features mentioned above with which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography for use in copying apparatuses and printers which photoconductor include a novel organic materials not used to date as a charge generating substance in the photosensitive layer, and has a high photosensitivity and excellent characteristics in repeated use.

In the first aspect of the present invention, a photoconductor for electrophotography comprises:

a substrate; and a photosensitive layer formed in the substrate and including at least one azulenium compound represented by the following general formula (I) or (II) as a charge generating substance:

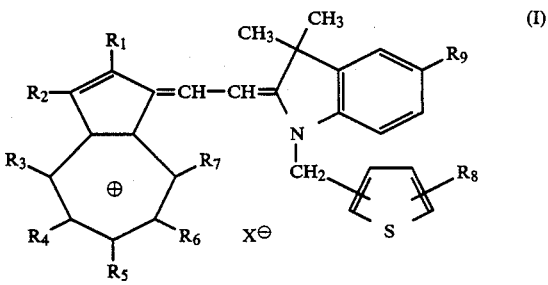

(I)

wherein, each of $R_1$ and $R_9$ stands for a hydrogen atom, a halogen atom, an alkoxy group, or an alkyl group or an aryl group, both of which may have a substituent(s), and $X^{\ominus}$ stands for an anion residual group;

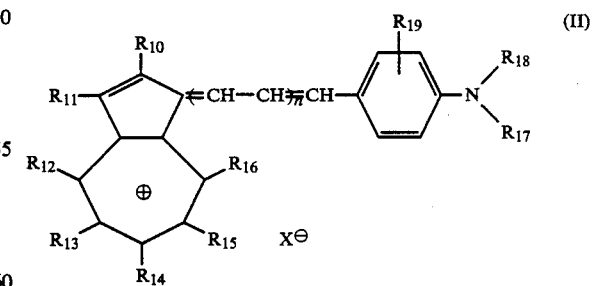

(II)

wherein, each of $R_{10}$ to $R_{19}$ stands for a hydrogen atom, a halogen atom, an alkoxy group, or an alkyl group which may have a substituent(s), each of $R_{17}$ and $R_{18}$ stands for an alkyl group, an aryl group, an alkenyl group, or an aralkyl group, each of which may have a substituent(s), and at least one of $R_{17}$ and $R_{18}$ stands for a thenyl group which may have a substituent(s), n stands for an integer of 0 or 1, and $X^\ominus$ stands for an anion residual group.

Here, the photosensitive layer may comprise a layer including dispersion of a charge generating substance selected from azulenium compounds represented by the general formula (I) or (II) and a charge transporting substance.

The photosensitive layer may comprise a laminate of a charge transporting layer mainly composed of a charge transporting substance and a charge generating layer including a compound selected from azulenium compounds represented by the general formula (I) or (II).

In the second aspect of the present invention, a photoconductor for electrophotography comprises:

a substrate; and a photosensitive layer formed on the substrate and including at least one azulenium compound represented by the following general formula (III) as a charge generating substance:

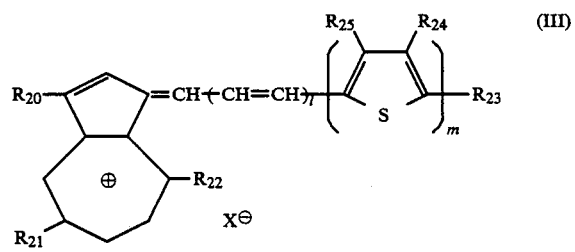

wherein, each of $R_{20}$, $R_{21}$ and $R_{22}$ stands for a hydrogen atom, a halogen atom, or an alkyl group, each of $R_{23}$, $R_{24}$ and $R_{25}$ stands for a hydrogen atom, a halogen atom, an alkyl group, an alkoxy group, a substituted or unsubstituted aryl group, or an amino group, l stands for an integer of 0 or 1, m stands for one integer from 0 to 5, and $X^\ominus$ stands for a pair ion.

Here, the photosensitive layer may comprise a layer including dispesion of a charge generating substance selected from azulenium compounds represented by the general formula (III) and a charge transporting substance.

The photosensitive layer may comprise a laminate of a charge transporting layer mainly composed of a charge transporting compound selected fro azulenium compounds represented by the general formula (III).

In the third aspect of the present invention, a photoconductor for electrophotography comprises:

a substrate; and a photosensitive layer formed on the substrate and including at least one azulenium compound represented by the following general formula (IV) as a charge generating substance:

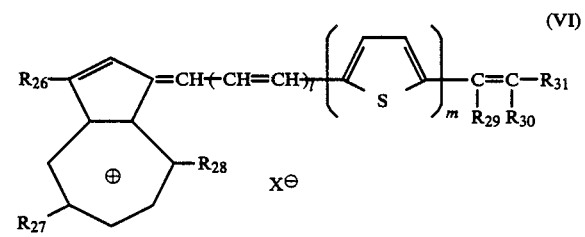

wherein, each of $R_{26}$, $R_{27}$, $R_{28}$, $R_{29}$ and $R_{30}$ stands for a hydrogen atom, a halogen atom, an alkyl group or an aryl group, $R_{31}$ stands for one of the formulae:

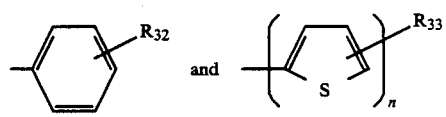

l stands for an integer of 0 or 1, m stands for an integer of 1 or 2, $X^\ominus$ stands for a pair ion, and in the structural formula of $R_{31}$, each of $R_{32}$ and $R_{33}$ stands for a hydrogen atom, a halogen atom, an alkyl group, a substituted or unsubstituted aryl group or an amino group, and n stands for an integer of 1 or 2.

Here, the photosensitive layer comprises a layer including dispersion of a charge generating substance selected from azulenium compounds represented by the general formula (IV) and a charge transporting substance.

The photosensitive layer comprise a laminate of a charge substance and a charger generating layer including a compound selected from azulenium compounds represented by the general formula (IV).

DETAILED DESCRIPTION OF PREFERRED EMBODIMENT

Figure 1:
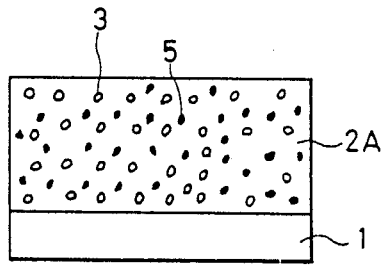
FIGS. 1 to 3 are schematic cross-sectional views of photoconductors according to the present invention, repectively.
Figure 2:
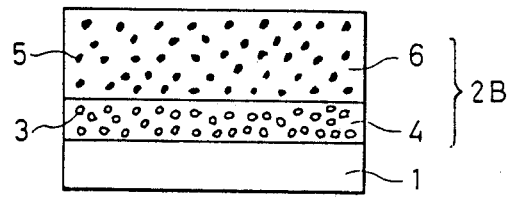
Figure 3:
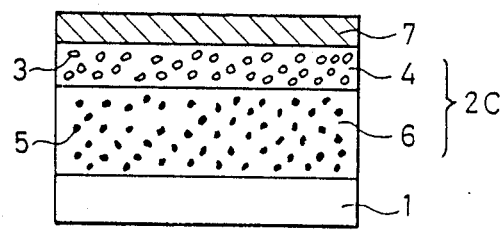

The photoconductor of the present invention, which contains an azulenium compound in the photosensitive layer thereof, may have any one of the structures as shown in FIGS. 1, 2 and 3 according to the manner of application thereto of the azulenium compound.

FIGS. 1, 2 and 3 are schematic cross-sectional views of different embodiments of the photoconductor of the present invention, respectively.

FIG. 1 shows a cross-sectional view of a monolayer type photoconductor. A photosensitive layer 2A is provided on an electroconductive substrate 1. The photosensitive layer 2A comprises an azulenium compound as a charge generating substance 3 and a charge transporting substance 5 both of which substances are dispersed in a resin binder matrix so that the photosensitive layer 2A functions as photoconductor.

FIG. 2 shows a cross-sectional view of a laminate type photoconductor. A laminated photosensitive layer 2B is provided on an electroconductive substrate 1, a lower layer of the laminate is a charge generating layer 4 including an azulenium compound 3 as a charge generating substance and an upper one is a charge transporting layer 6 containing a charge transporting substance 5 as a main component, so that the photosensitive layer 2B functions as a photoconductor. This photoconductor is usually used according to the negative charge mode.

FIG. 3 shows a cross-sectional view of another laminate type photoconductor having a layer structure in reverse to that of FIG. 2. A laminated photosensitive layer 2C is provided on an electroconductive substrate 1, a lower layer of the laminate is a charge transporting layer 6 and an upper one is a charge generating layer 4 including an azulenium compound as a charge generating substance 3. The photosensitive layer also functions as a photoconductor. This photoconductor is usually used according to the positive charge mode In this case, a covering layer 7 may generally be further provided as shown in FIG. 3 to protect the charge generating layer 4.

Thus, two kinds of layer structure are provided for laminate type photoconductors. The reason for this is that, even if any photoconductor with the layer structure as shown in FIG. 2 is to be used in the positive charge mode, no charge transporting substances adaptable to the positive charge mode have been found yet. Accordingly, when any laminate type photoconductor is to be used in the positive charge mode, the photoconductor is required of a layer structure as shown in FIG. 3 for the present.

A photoconductor as shown in FIG. 1 can be produced by dispersing a charge generating substance in a solution of a charge transporting substance and a resin binder and applying the resulting dispersion on an electroconductive substrate and then drying the resulting coating film.

A photoconductor as shown in FIG. 2 can be prepared by applying and drying a dispersion of a particulate charge generating substance in a solvent and/or a resin binder on an electroconductive substrate, followed by applying a solution of a charge transporting substance and a resin binder on the resulting layer and drying.

A photoconductor as shown in FIG. 3 can be prepared by applying and drying a solution of a charge transporting substance and a resin binder onto an electroconductive substrate, and coating and drying a dispersion of a particulate charge generating substance in a solvent and/or a resin binder onto the resulting coating layer, followed by formation a covering layer.

The electroconductive substrate 1 serves as an electrode of the photoconductor and a a support for a layer(s) formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of an azulenium compound as a charge generating substance 3 in a resin binder, and this layer generates an electric charge upon receiving light. It is important that the charge generating layer 4 be high not only in charge generating efficiency but also in capability of injecting the generated electric charge into the charge transporting layer 6 and any covering layer 7, which capability is desirably as little dependent upon the electric field as possible and high even in low intensity electric fields. It also is possible to form a charge generating layer using a charge generating substance as a main component in mixture with a charge transporting substance and so on. Resin binders usable in the charge generating layer include polycarbonates, polyesters, polyamides, polyurethanes, epoxy resins, silicone resins, and homopolymers and copolymers of methacrylic esters, which may be used either alone or in appropriate combination.

The charge transporting layer 6, which is formed by application of a solution or dispersion of a hydrazone compound, a pyrazoline compound, a stilbene compound, a tri-phenyl-amine compound, an oxazole compound or an oxadiazole compound as an organic charge transporting substance in a resin binder, exhibits a function of serving as an insulating layer in the dark to retain an electric charge of the photoconductor as well as a function transporting an electric charge injected from the charge generating layer upon receiving light. Resin binders usable in the charge transporting layer include polycarbonates, polyesters, polyamides, polyurethanes, epoxy resins, silicone resins, and homopolymers and copolymers of methacrylic ester.

The covering layer 7 has a function of receiving and retaining an electric charge generated by corona discharge in the dark and a capability of transmitting light to which the charge generating layer should respond. It is necessary that the covering layer 7 transmits light upon exposure of the photoconductor and allows the light to reach the charge generating layer, and then undergoes the injecting of an electric charge generated in the charge generating layer to neutralize and erases a surface electric charge. Materials usable in the covering layer include organic insulating film-forming materials such as polyesters and polyamide. Such organic materials may also be used in mixture with an inorganic material such as a glass resin or $SiO_2$, or an electric resistance-lowering material such as a metal or a metallic oxide. Materials usable in the covering layer are not limited to organic insulating film-forming materials, and further include inorganic materials such as $SiO_2$, metals, and metallic oxides, which may be formed into a covering layer by an appropriate method such a vacuum evaporation and deposition, or sputtering. From the viewpoint of the aforementioned description, it is desirable that the material to be used in the covering layer be as transparent as possible in the wavelength range wherein the charge generating substance attains maximum light absorption.

Although the thickness of the covering layer depends on the material or composition thereof, it can be arbitrarily set in so far as it does not produce any adverse effects including an increase in a residual potential in continuous repeated use.

The first group of azulenium compounds to be used in the present invention is represented by the following general formula (I).

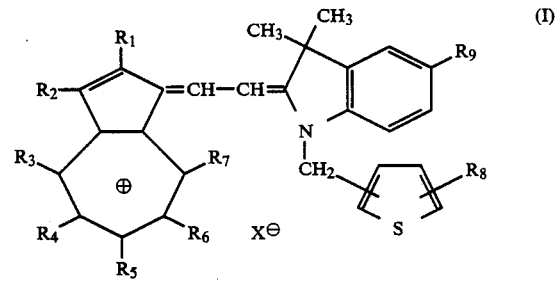

Wherein, each of $R_1$ to $R_9$ stands for a hydrogen atom, a halogen atom, and an alokoxy group, or an alkyl group, an aryl group, both of which may have a substituent(s), and $X^\ominus$ stands for an anion residual group.

These azulenium compounds represented by the general formula (I) can be readily synthesized by reacting a compound of the formula

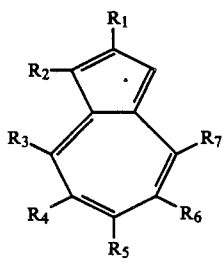
with an aldehyde compound of the formula
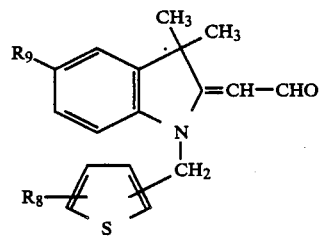
in an appropriate organic solvent such as tetrahydrofuran in the presence of a corresponding ion species.
Specific examples of the azulenium compounds of the general formula (I) prepared in the above-mentioned manner include:
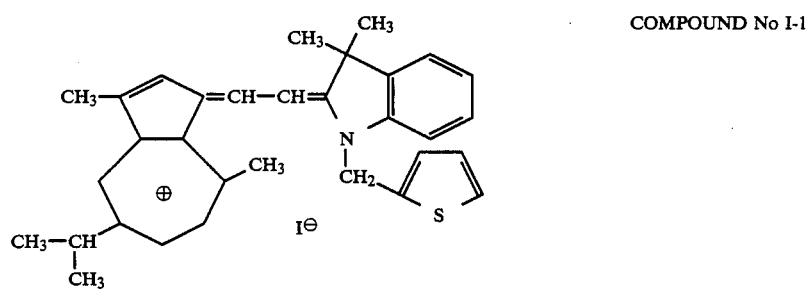
COMPOUND No I-1
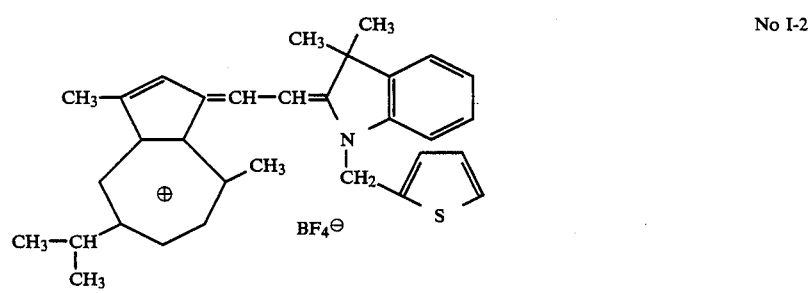
No I-2
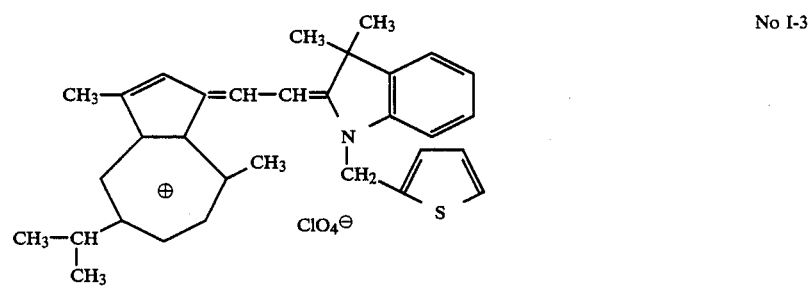
No I-3
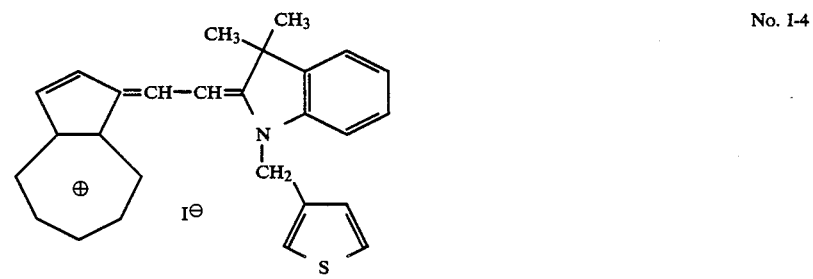
No. I-4

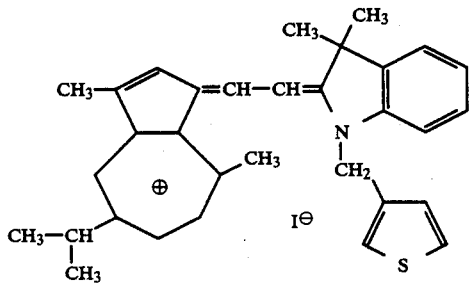 No I-5
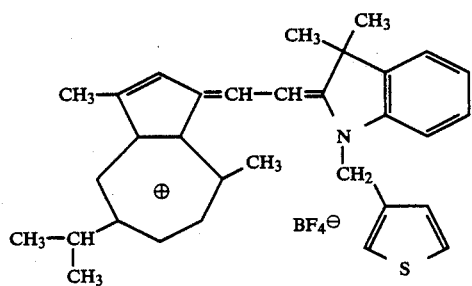 No I-6
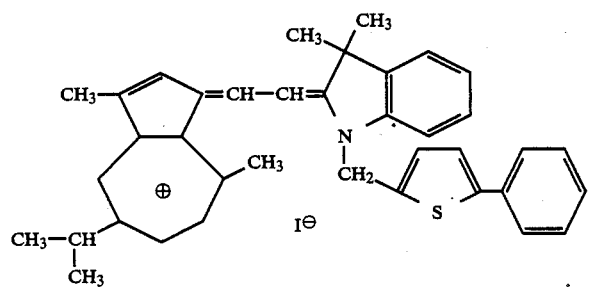 No I-7
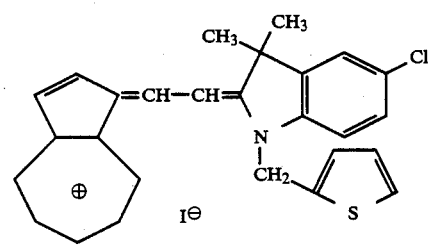 No I-8
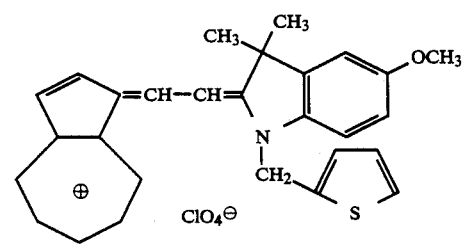 No I-9
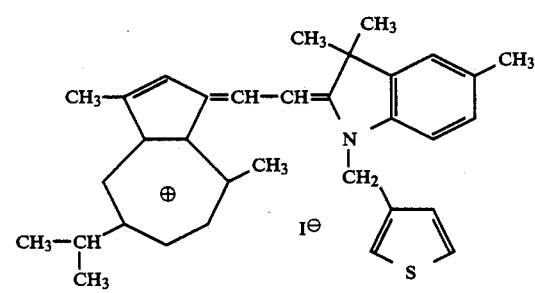 No I-10

-continued
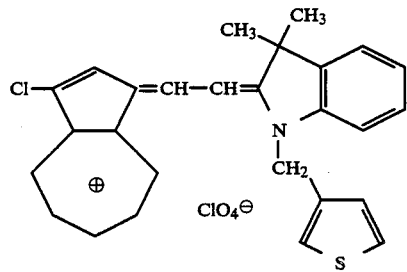 No I-11
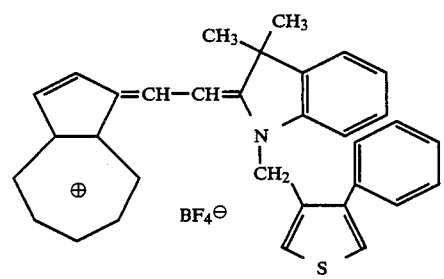 No I-12
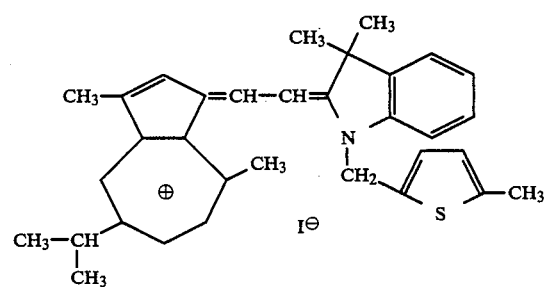 No I-13
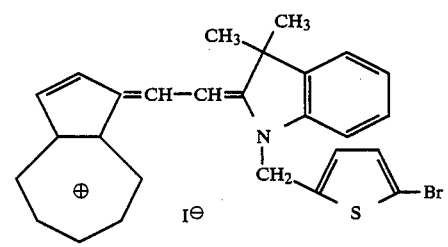 No I-14
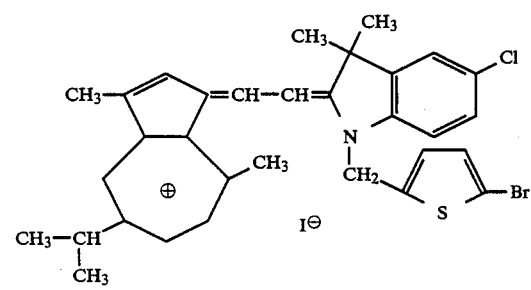 No I-15
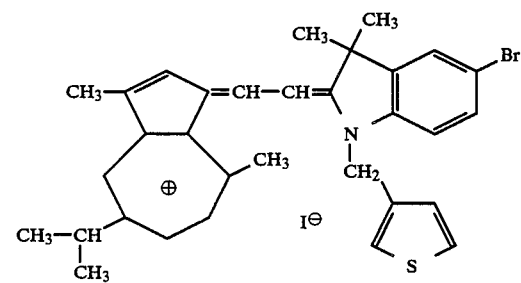 No I-16

-continued

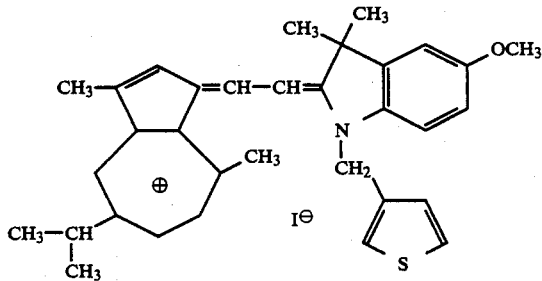

No I-17

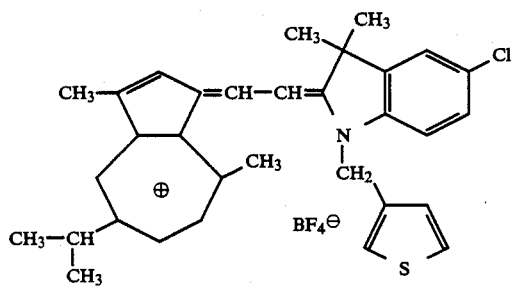

No I-18

The second group of azulenium compounds to be used in the present invention is represented by the following general formula (II).

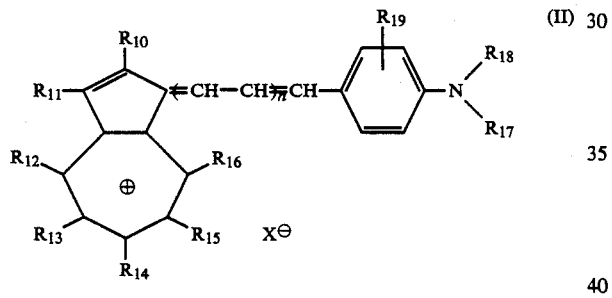
(II)

Wherein, each $R_{10}$ to $R_{16}$ and $R_{19}$ stands for a hydrogen atom, a halogen atom, an alkoxy group or an aklyl group which may have a substituent(s), each of $R_{17}$ and $R_{18}$ stands for an alkyl group, an aryl group, an alkenyl group or an aralkyl group, each of which may have a substituent(s), and further at least one of $R_{17}$ and $R_{18}$ stands for a thenyl group which may have a substituent(s), n stand for an integer of 0 to 1, and $X^\ominus$ stands for an anion residual group.

These azulenium compound represented by the general formula (II) can be easily synthesized by reacting a compound of the formula

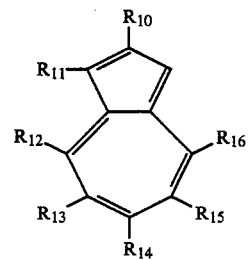

with an aldehyde compound of the formula

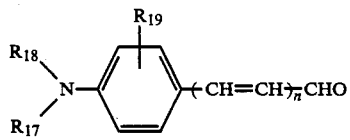

in an appropriate organic solvent such as tetrahydrofuran in the presence of a corresponding ion species.

Specific examples of the azulenium compounds of the general formula (II) prepared in the above-mentioned manner include:

COMPO
No II-1

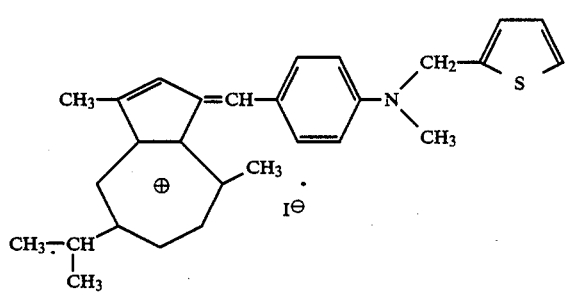

-continued
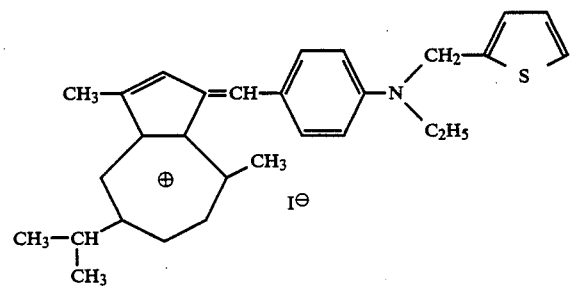
No II-2
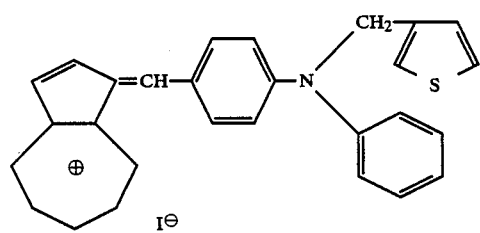
No II-3
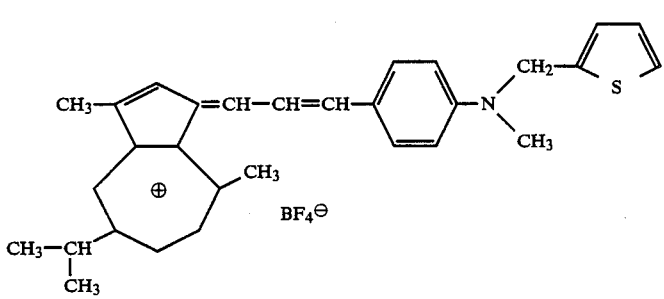
No II-4
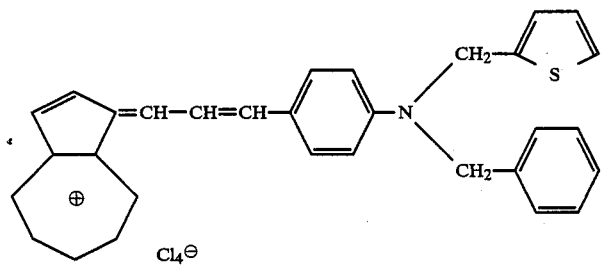
No II-5
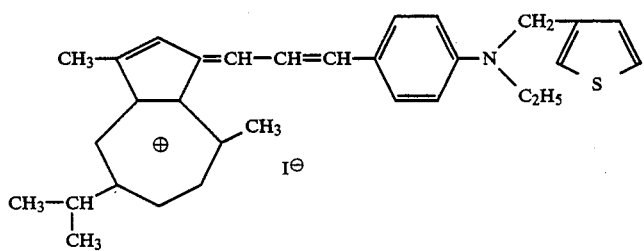
No II-6
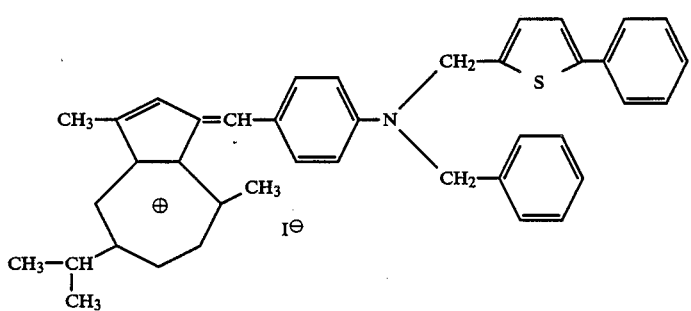
No II-7

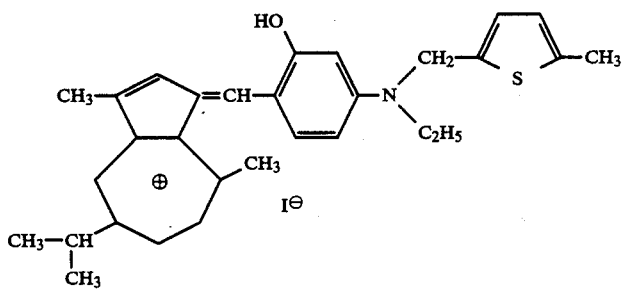
No II-8
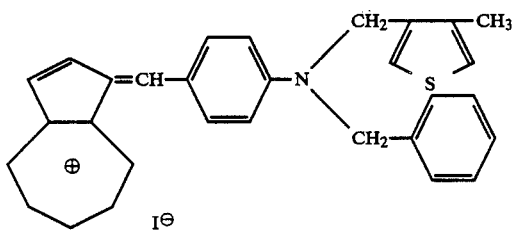
No II-9
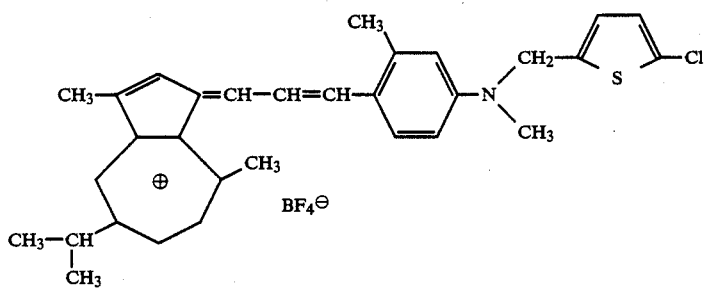
No II-10
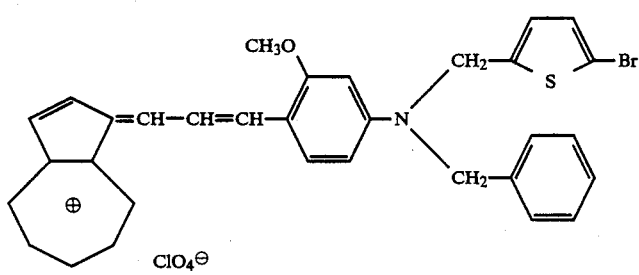
No II-11
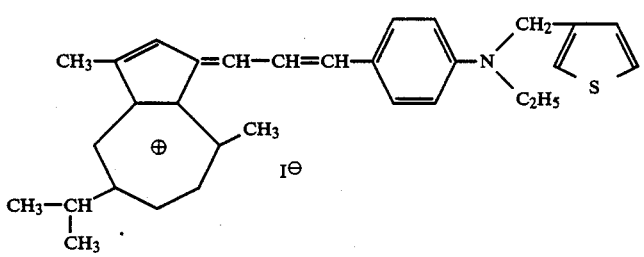
No II-12

-continued
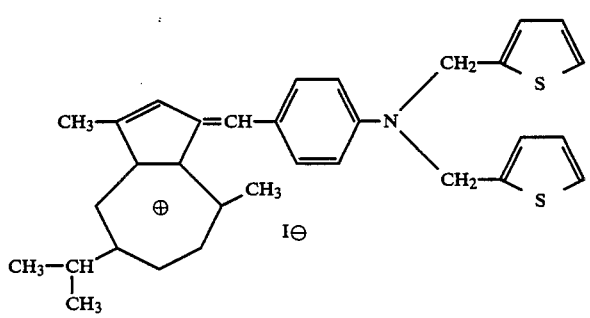
No II-13
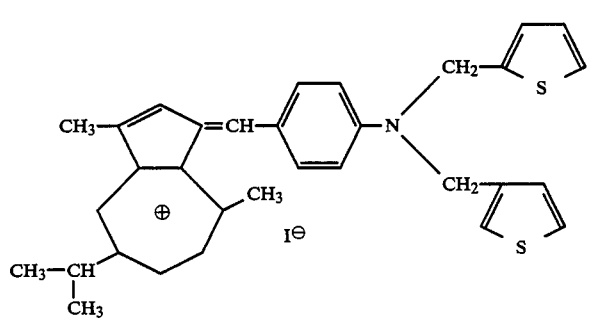
No II-14
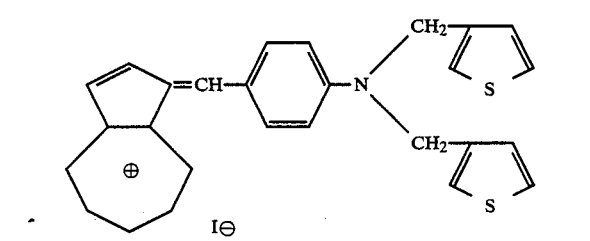
No II-15
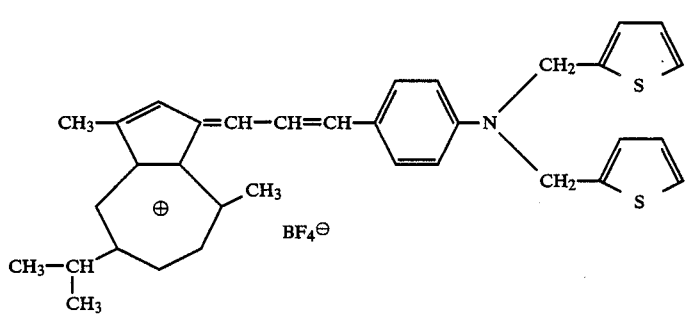
No II-16
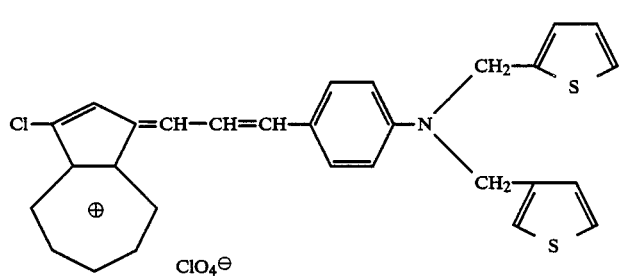
No II-17

-continued

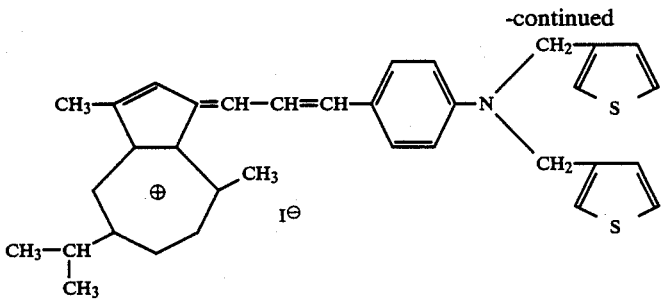

No II-18

Examples will now be given, wherein various compounds represented by the general formula (I) or (II) were respectively used to produce photoconductors.

EXAMPLE I-1

50 parts by weight of the azulenium compound No. 1-1, 100 parts by weight of a polyester resin (Vylon 200, manufactured by Toyobo Co., Ltd.) and 100 parts by weight of 1-phenyl-3-(p-diethylaminostyryl)-5-(p-diethylaminophenyl)-2-pyrazoline (ASPP) are kneaded with tetrahydrofuran (THF) as a solvent with a mixer for 3 hours to prepare a coating liquid. The coating liquid was applied onto an aluminum-deposited polyester film (Al-PET) as an electroconductive substrate by means of the wire bar technique to form a photosensitive layer having a dry thickness of 15 μm. Thus, a photoconductor with the structure shown in FIG. 1 was produced.

EXAMPLE I-2

The photoconductor was produced in the same manner as in Example I-1 except that the compound No. II-1 was used instead of the compound No. I-1 in Example I-1.

EXAMPLE I-3

First, a solution of 100 parts by weight of p-diethylaminobenzaldenyde-diphenylhydrazone (ABPH) in 700 parts by weight of tetrahydrofuran (THF) was mixed with a solution of 100 parts by weight of polycarbonate resin (Panlite L-1250) in 700 part by weight of mixed solvent including the same parts of THF and dichloromethane to prepare a coating liquid. The coating liquid was applied onto an aluminum-deposited polyester film substrate by the wire bar technique to form a charge transporting layer having a dry thickness of 15 μm. 50 parts by weight of the compound No. I-1, 50 parts by weight of a polyester resin (Vylon 200), and 50 parts by weight of PMMA were kneaded with a mixer for 3 hours together with THF as a solvent to prepare a coating liquid, which was then applied onto the charge transporting layer by the wire bar technique to form a charge generating layer having a dry thickness of 0.5 μm. Thus, a photoconductor with a structure corresponding to that shown in FIG. 3 was produced. The covering layer was not provided because it was not related to the present invention.

EXAMPLE I-4

The photoconductor was produced in the same manner as in Example I-3 except that the compound No. II-1 was used instead of the compound No. I-1.

EXAMPLES I-5 and I-6

A charge transporting layer was formed in substantially the same manner as in Example I-3 or I-4 except that α-phenyl-4'-N,N-dimethylaminostilbene, which is a stilbene compound, was used to replace ABPH as a charge transporting substance in the Example I-3 or I-4. Then a charge generating layer was formed on the charge transporting layer, thus the photoconductor of Examples I-5 and I-6 were produced.

EXAMPLES I-7 and I-8

A charge transporting layers were formed in substantially the same manner as in Examples I-3 and I-4 except that tri(p-toryl)amine, which is a triphenylamine compound, was used to replace ABPH a a charge transporting substance in the Example I-3 and I-4. Then a charge generating layers were formed on the respective charge transporting layers, thus the photoconductors of Examples I-7 and I-8 were produced.

EXAMPLES I-9 and I-10

A charge transporting layers were formed in substantially the same manner as in Example I-3 and I-4 except that 2,5-bis(p-diethylaminophenyl)-1,3,4-oxadiazole, which is an oxadiazole compound, was used to replace ABPH as a charge transporting substance in the Example I-3 and I-4. Then a charge generating layers were formed on the respective charge transporting layer, thus the photoconductors of Examples I-9 and I-10 were produced.

The electrophotographic characteristics of the ten photoconductors thus produced were measured by utilizing an electrostatic recording paper testing apparatus (Kawaguchi Denki Model SP-428).

The surface potential $V_s$ (volt) of each photoconductor is an initial surface potential which was measured when the surface of the photoconductor was positively charged in the dark by corona discharge at +6.0 kV for 10 seconds. After the discontinuation of the corona discharge, the photoconductor was allowed to stand in the dark for 2 seconds, after which the surface potential $V_d$ (volts) of the photoconductor was measured. Subsequently, the surface of the photoconductor was irradiated with white light at an illuminance of 2 luxes and the time (seconds) required for the irradiation to decrease the surface potential of the photoconductor to half of the $V_d$ was measured, then from which time and the illuminance the half decay exposure amount $E_{\frac{1}{2}}$ (lux·sec) was calculated. Also, the surface potential of the photoconductor after 10 seconds of irradiation thereof with white light at an illuminance of 2 luxes was measured as a residual potential $V_r$ (volts).

TABLE 1

| Example | $V_s$ (volt) | $V_r$ (volt) | $E_{\frac{1}{2}}$ (lux · sec) |
|---|---|---|---|
| I-1 | 580 | 130 | 7.1 |
| I-2 | 550 | 110 | 8.0 |

TABLE 1-continued

| Example | $V_s$ (volt) | $V_r$ (volt) | $E_{\frac{1}{2}}$ (lux · sec) |
|---|---|---|---|
| I-3 | 640 | 80 | 5.9 |
| I-4 | 600 | 90 | 5.9 |
| I-5 | 660 | 100 | 6.1 |
| I-6 | 630 | 100 | 6.6 |
| I-7 | 600 | 70 | 6.7 |
| I-8 | 620 | 80 | 6.1 |
| I-9 | 610 | 70 | 6.3 |
| I-10 | 660 | 60 | 6.7 |

As can be seen in Table 1, the photoconductors of Examples I-1 to I-10 have good characteristics in the surface potentials $V_s$, the half decay exposure amounts $E_{\frac{1}{2}}$ and the residual potentials $V_r$.

EXAMPLE I-11

100 parts by weight of each of respective compounds Nos. from I-2 to I-18, Nos. II-2 to II-18 and 100 parts by weight of polyester resin (Vylon 200) were kneaded with THF as a solvent with a mixer for 3 hours to prepare a coating liquid. The respective coating liquids were applied onto aluminum substrates to form a charge generating layer having a dry thickness of about 0.5 μm. Further, the coating liquid prepared in substantially the same manner as in Example I-3, except that the ASPP was used instead of ABPH as a charge transporting substance, was applied on the respective charge generating layer having a thickness of about 15 μm, thus photoconductors were produced.

The electrophotographic characteristics of the photoconductors thus produced were measured by utilizing an electrostatic recording paper testing apparatus SP-428. The results of the measurements are shown in Table 2. The results are obtained as follows. The surface potential $V_s$ (volts) of a photoconductor was measured when the surface of a photoconductor was negatively charged at $-6.0$ kV for 10 seconds. Subsequently, the photoconductor was allowed to stand in the dark for 2 second after the discontinuation of the corona discharge. Thereafter, the surface of the photoconductor was irradiated with white light at an illuminance of 2 luxes and the time (seconds) required to reduce the surface potential of the photoconductor to a half of the $V_d$ was measured, then from which the half decay exposure amount $E_{\frac{1}{2}}$ (lux·sec) was calculated.

TABLE 2

| Compound No. | $E_{\frac{1}{2}}$ (lux · sec) | Compound No. | $E_{\frac{1}{2}}$ (lux · sec) |
|---|---|---|---|
| I-2 | 6.2 | II-2 | 5.1 |
| I-3 | 6.9 | II-3 | 6.2 |
| I-4 | 6.2 | II-4 | 6.8 |
| I-5 | 5.9 | II-5 | 4.7 |
| I-6 | 6.8 | II-6 | 6.3 |
| I-7 | 6.3 | II-7 | 6.5 |
| I-8 | 6.8 | II-8 | 6.2 |
| I-9 | 8.1 | II-9 | 8.0 |
| I-10 | 7.9 | II-10 | 4.9 |
| I-11 | 6.5 | II-11 | 6.2 |
| I-12 | 6.9 | II-12 | 6.1 |
| I-13 | 6.6 | II-13 | 7.1 |
| I-14 | 8.0 | II-14 | 8.2 |
| I-15 | 6.7 | II-15 | 6.8 |
| I-16 | 6.3 | II-16 | 5.2 |
| I-17 | 5.9 | II-17 | 4.8 |
| I-18 | 5.9 | II-18 | 5.0 |

As can be seen in Table 2, the photoconductors using the respective compounds No. I-2 to No I-18, Compounds No. II-2 to No. II-18 were satisfactory with respect to the half decay exposure amounts.

The third group of azulenium compounds to be used in the present invention is represented by the following general formula (III).

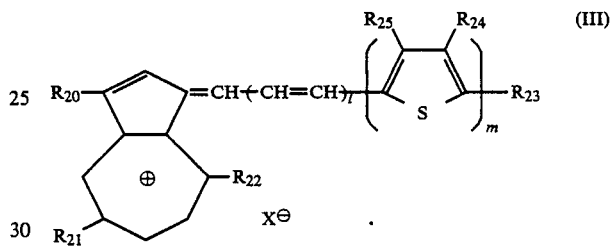

Wherein, each of $R_{20}$, $R_{21}$ and $R_{22}$ stands for a hydrogen atom, a halogen atom or an alkyl group, each $X_{23}$, $X_{24}$ and $X_{25}$ stands for a hydrogen atom, a halogen atom, an alkyl group, an alkoxy group, or an aryl group or an amino group both of which may have or may not have a substituent(s), l stand for an integer of 0 to 1, m stands for one integer from 0 to 5, and $X^{\ominus}$ stands for a pair ion.

These azulenium compounds represented by the general formula (III) can be easily synthesized by reacting a compound of the formula:

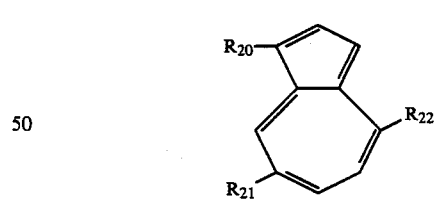

with an aldehyde compound of the formula

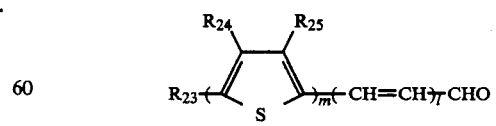

in the appropriate organic solvent such as tetrahydrofuran in the presence of a corresponding pair ion species.

Specific examples of the azulenium compounds of the generally formula (III) prepared in the above-mentioned manner include:

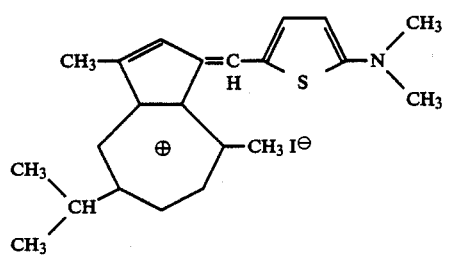
COMPOUND No III-1
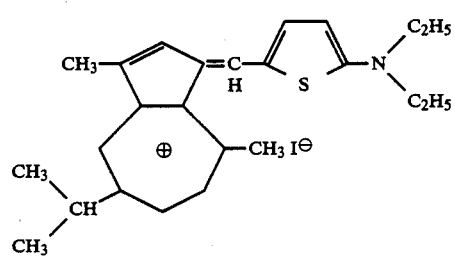
COMPOUND No III-2
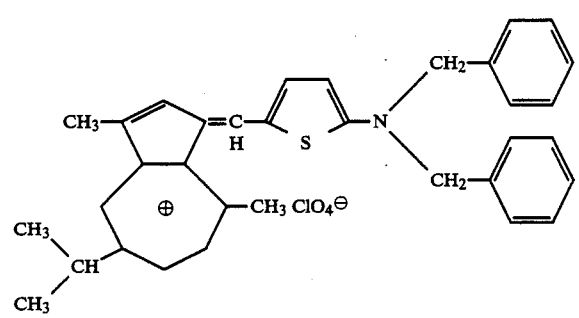
COMPOUND No III-3
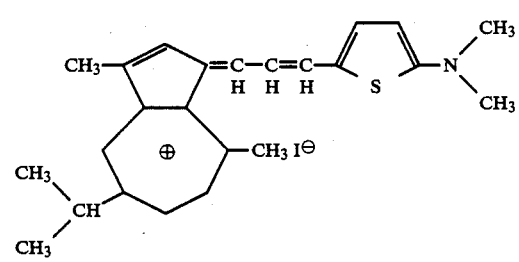
COMPOUND No III-4
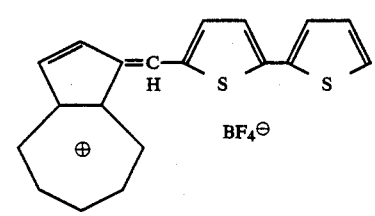
COMPOUND No III-5
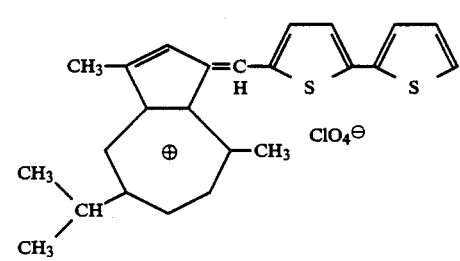
COMPOUND No III-6

-continued
COMPOUND No III-7
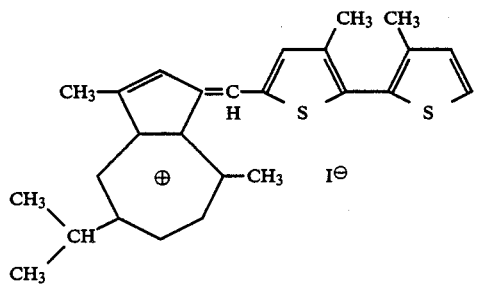
COMPOUND No III-8
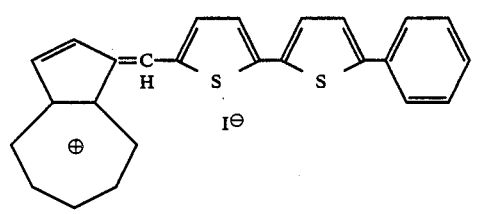
COMPOUND No III-9
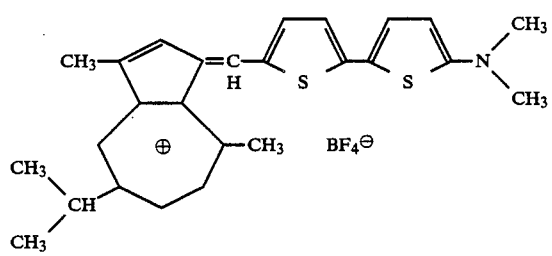
COMPOUND No III-10
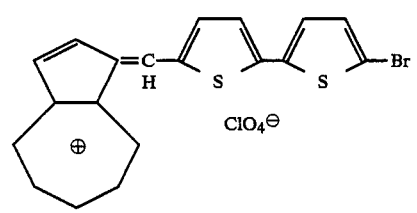
COMPOUND No III-11
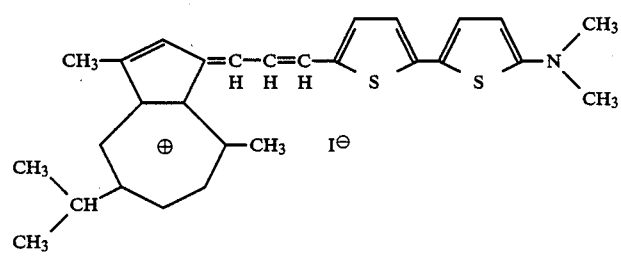
COMPOUND No III-12
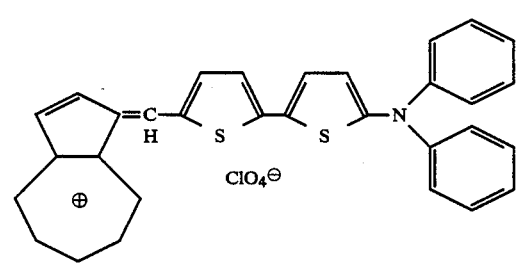

-continued
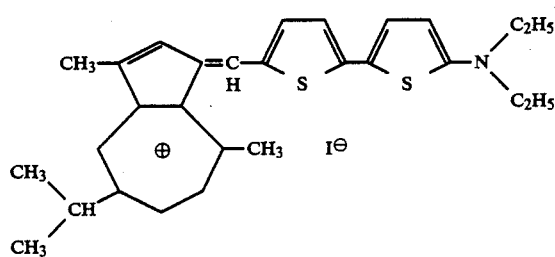
COMPOUND No III-13
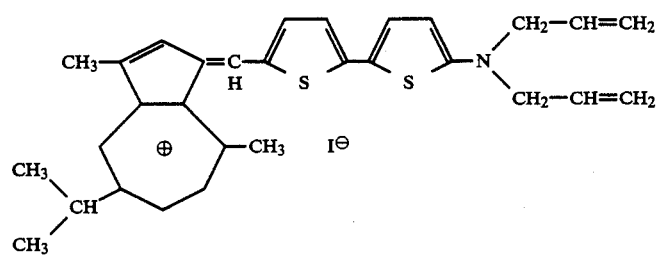
COMPOUND No III-14
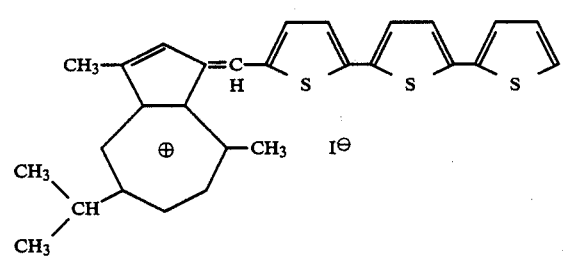
COMPOUND No III-15
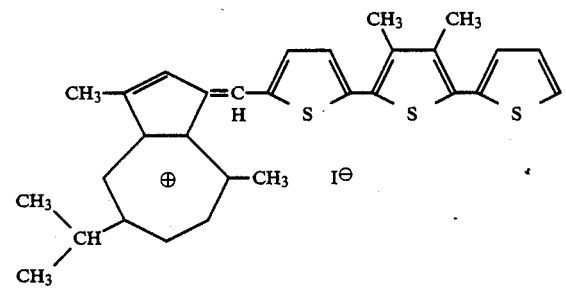
COMPOUND No III-16
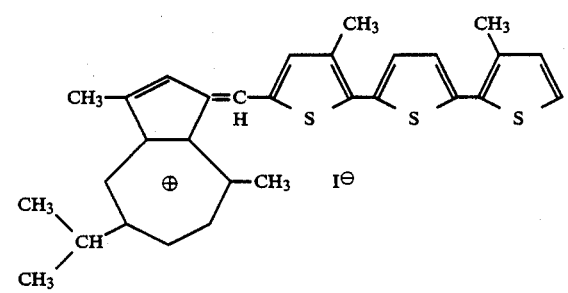
COMPOUND No III-17
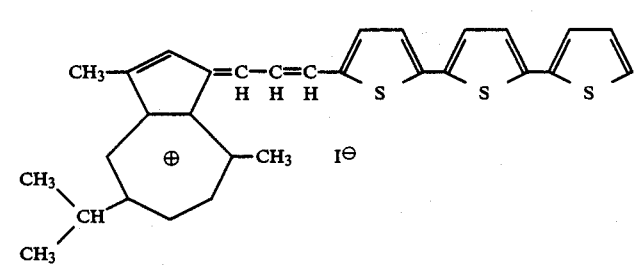
COMPOUND No III-18

-continued
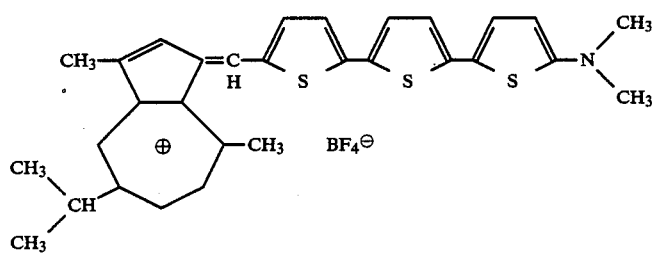
COMPOUND No III-19
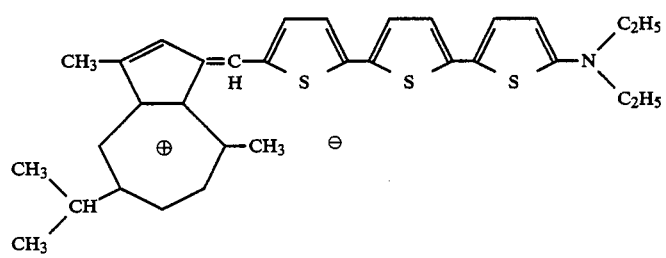
COMPOUND No III-20
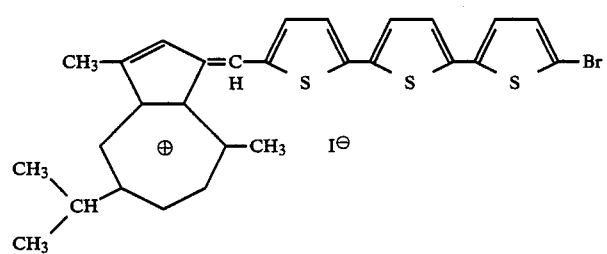
COMPOUND No III-21
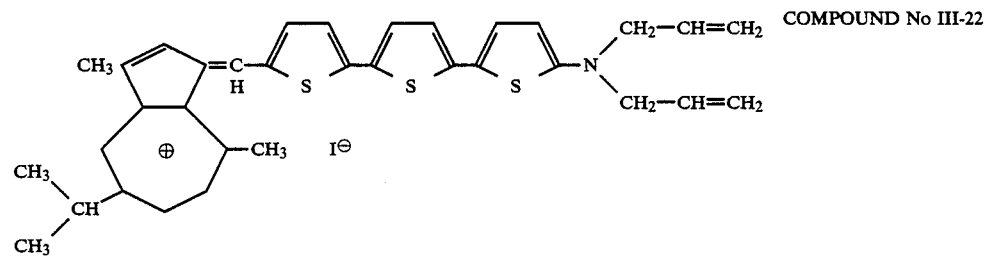
COMPOUND No III-22
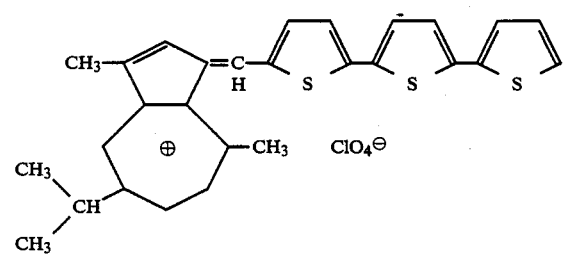
COMPOUND No III-23
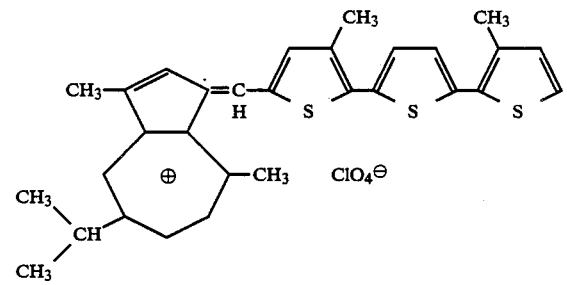
COMPOUND No III-24

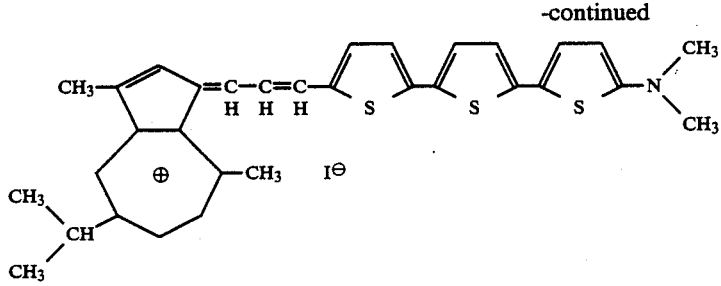

COMPOUND No III-25

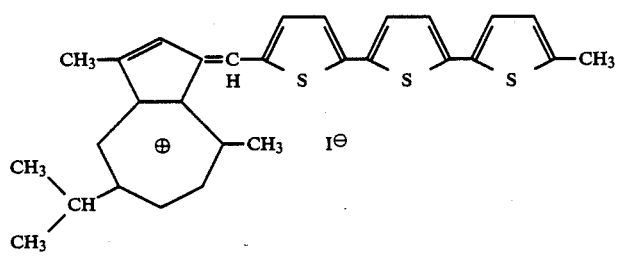

COMPOUND No III-26

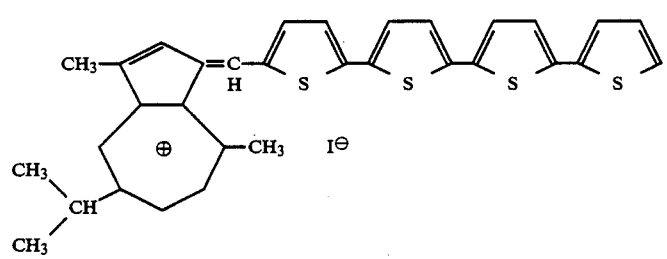

COMPOUND No III-27

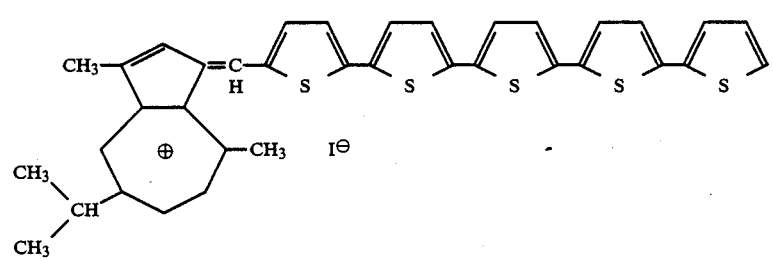

COMPOUND No III-28

The fourth group of azulenium compounds to be used in the present invention is represented by the following general formula (IV).

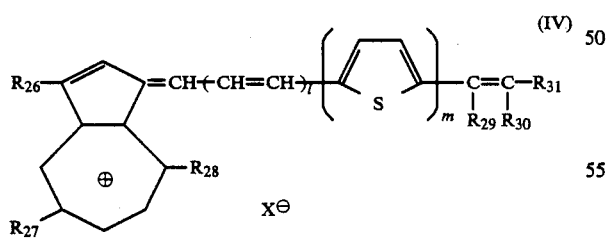

Wherein, each $X_{26}$, $X_{27}$, $X_{28}$, $X_{29}$ and $X_{30}$ stands for a hydrogen atom, a halogen atom, an alkyl group, or an aryl group, $R_{31}$ stands for one of the following formulae $l$ stands for an integer of 0 or 1, m stands for an integer of 1 or 2, $X^R$ stands for a pair ion, each of $R_{32}$ and $R_{33}$ stands for a hydrogen atom, a halogen atom, an alkyl group, or an aryl group or an amino group both of which may have or may not have a substituent(s), and n stands for an integer of 1 or 2.

These azulenium compounds represented by the general formula (IV) can be easily synthesized by reacting a compound of the formula:

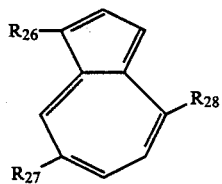
with a corresponding aldehyde compound of the formula:
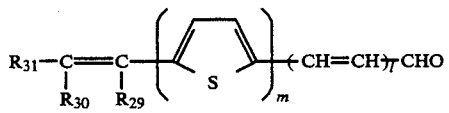
in an appropriate organic solvent such as tetrahydrofuran in the presence of a corresponding ion species.
Specific examples of the azulenium compounds of the general formula (IV) prepared in the above-mentioned manner include.
COMPOUND
No III-31
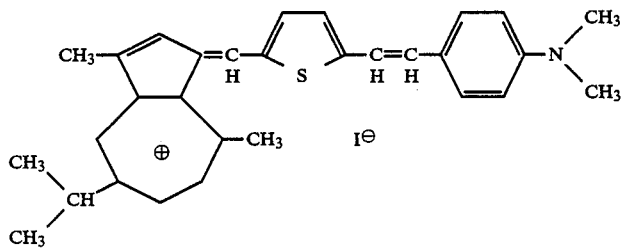
No III-32
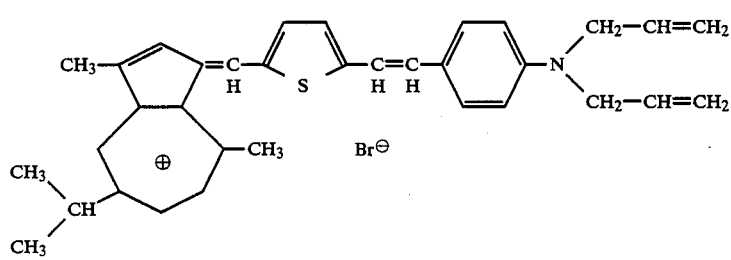
No III-33
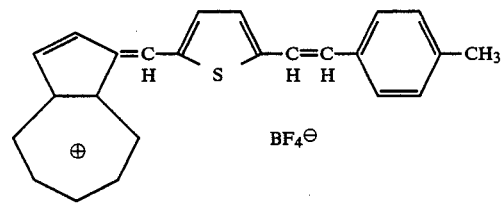
No III-34
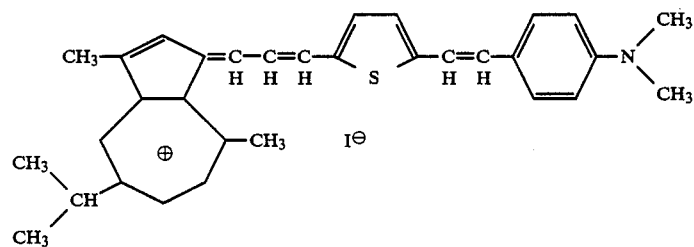
No III-35
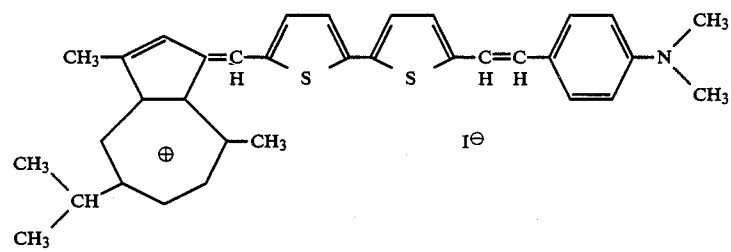

| | COMPOUND |
|---|---|
| 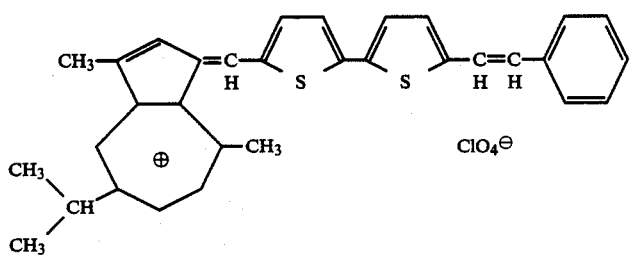 | No III-36 |
| 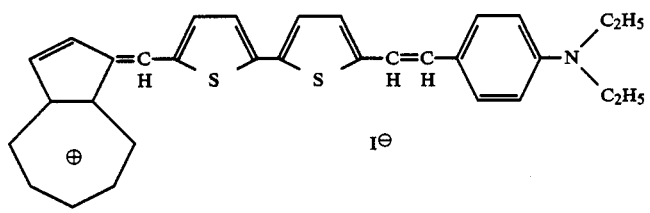 | No III-37 |
| 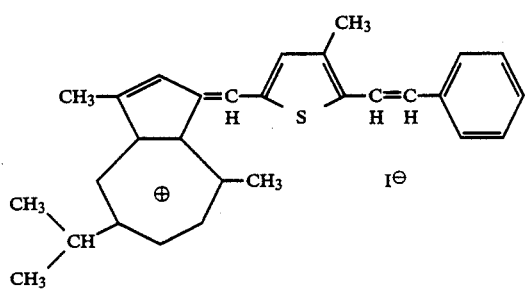 | No III-38 |
| 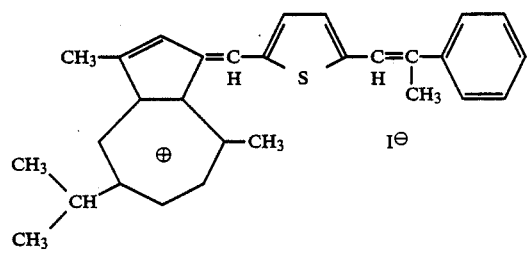 | No III-39 |
| 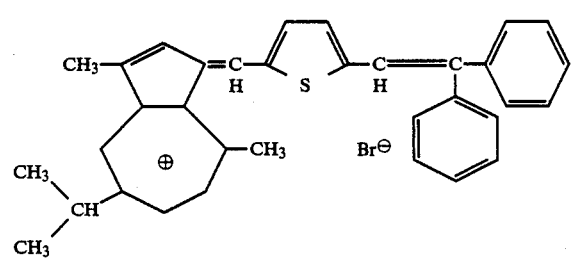 | No III-40 |
| 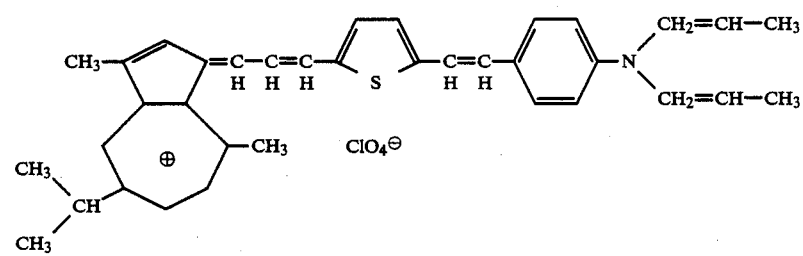 | No. III-41 |

-continued
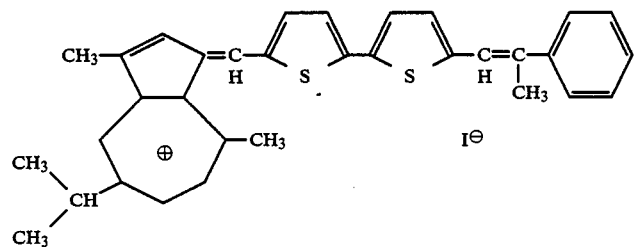
COMPOUND
No. III-42
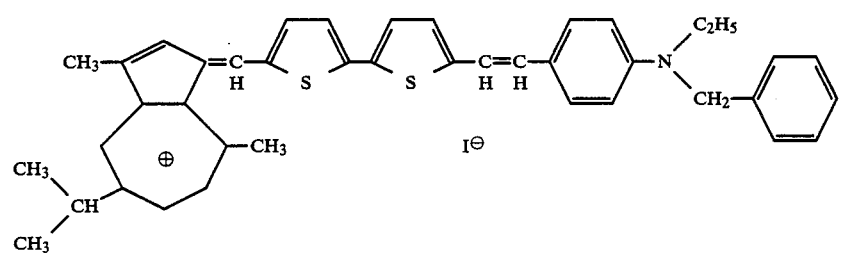
No III-43
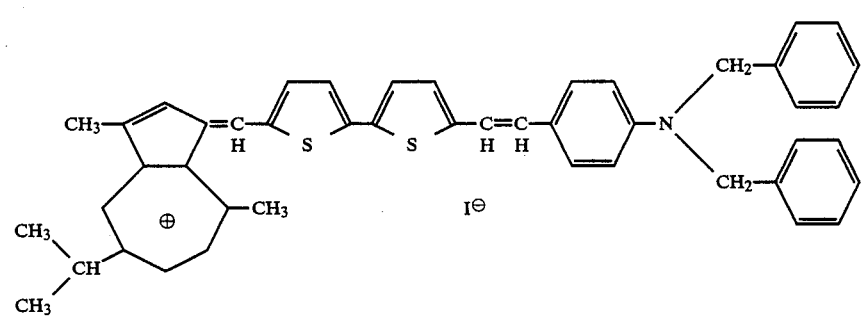
No III-44
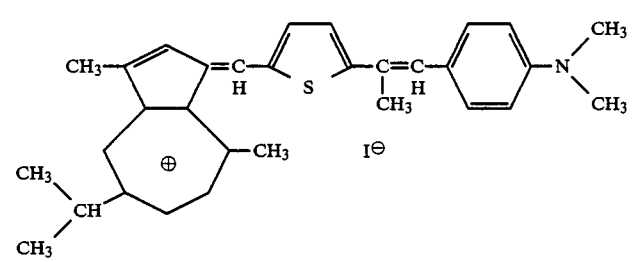
No III-45
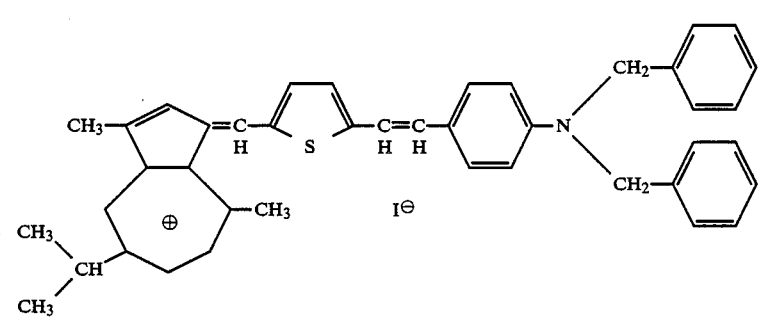
No III-46
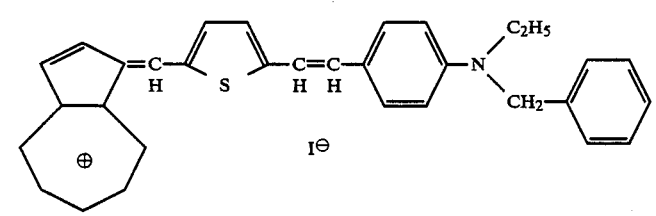
No III-47

-continued
| | COMPOUND |
|---|---|
| 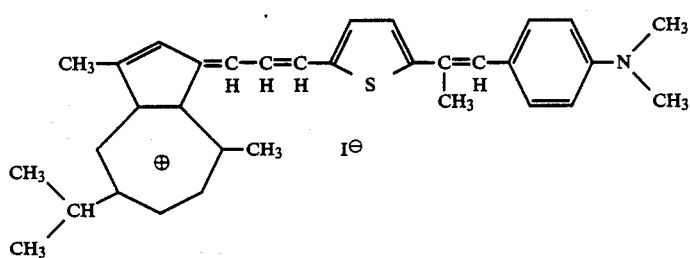 | No III-48 |
| 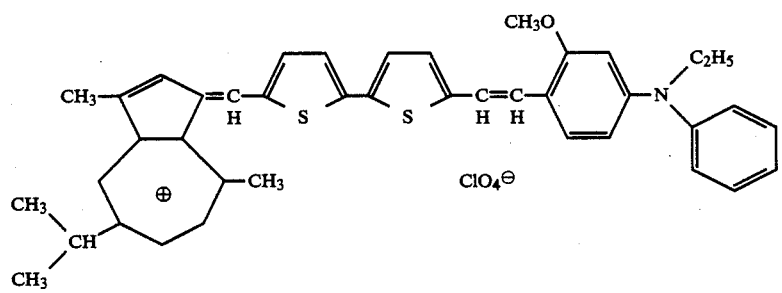 | No III-49 |
| 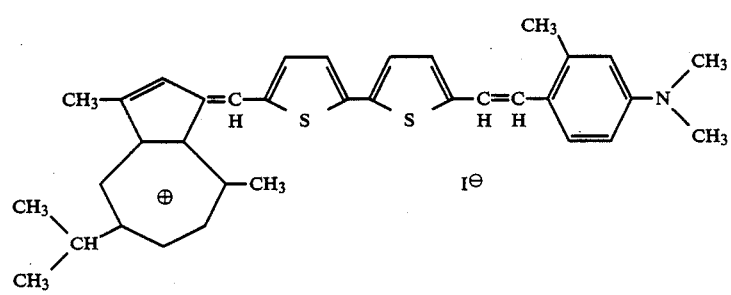 | No III-50 |
| 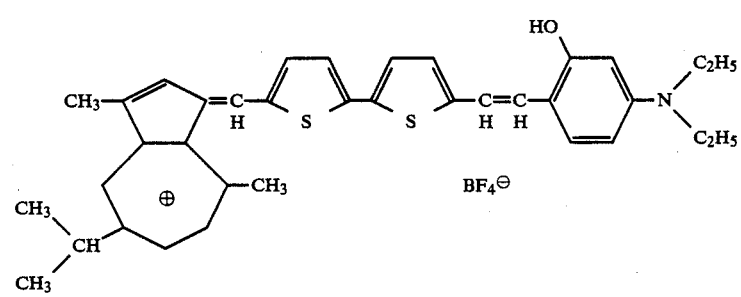 | No III-51 |
| 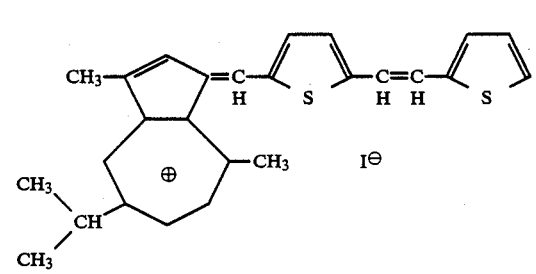 | No III-52 |
| 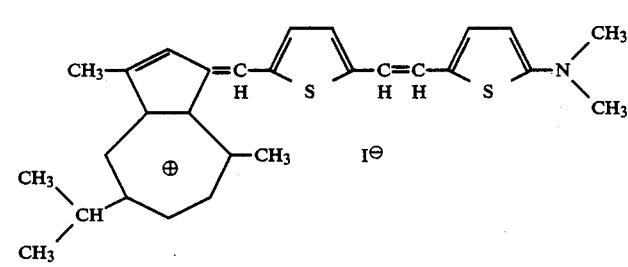 | No III-53 |

COMPOUND
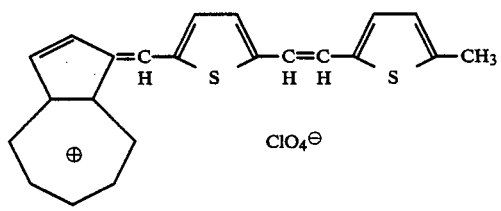
No III-54
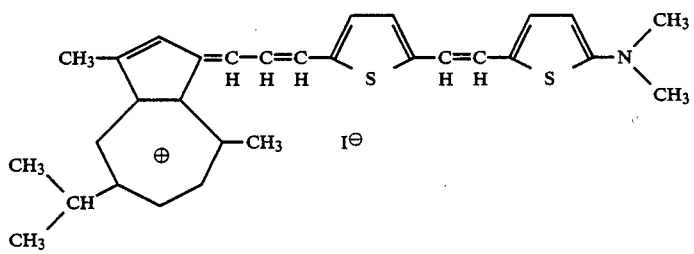
No III-55
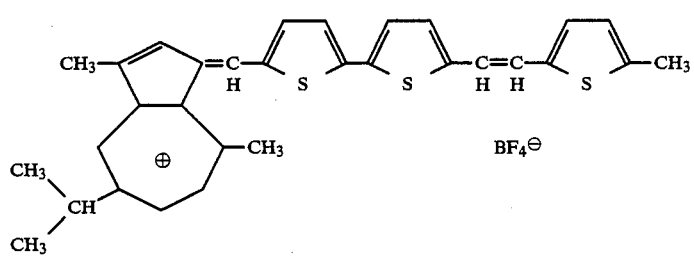
No III-56
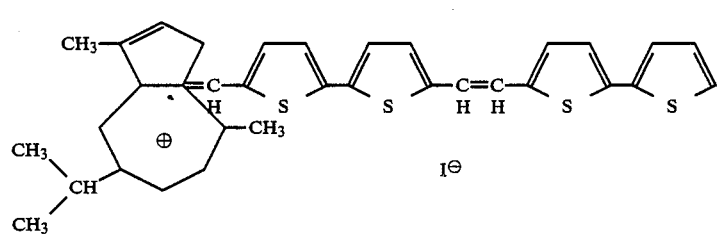
No III-57
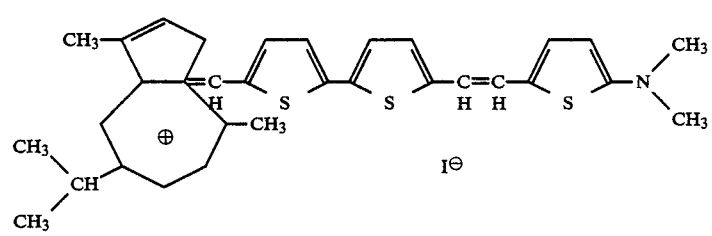
No III-58
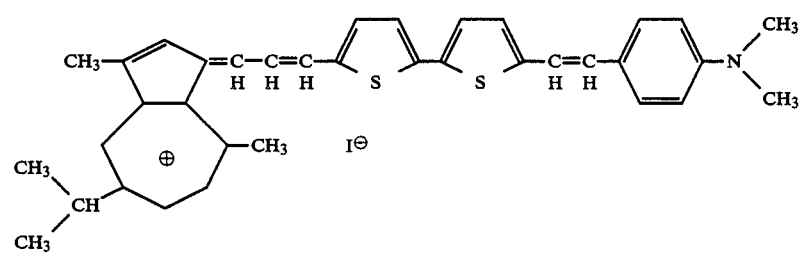
No III-59

COMPOUND No III-60

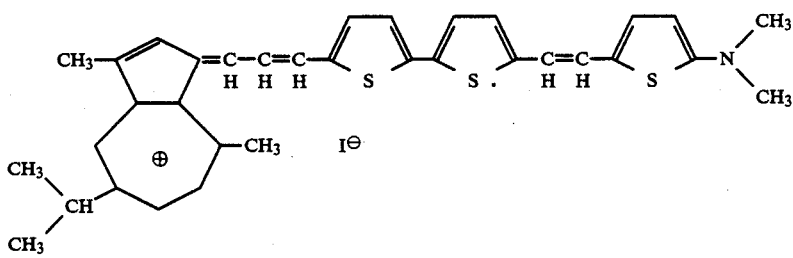

Examples will now be given, wherein various compounds represented by the general formula (III) or (IV) were respectively used to produce photoconductors.

EXAMPLE II-1

A photoconductor having the structure shown in FIG. 1 and comprising a photosensitive layer having a thickness of 15 μm was produced in substantially the same manner as in Example I-1 except that the compound No. III-1 mentioned above was used instead of the compound No. I-1.

EXAMPLE II-2

Further, 100 parts by weight of p-diethylaminobenzaldehyde-diphenylhydrazone (ABPH) and 100 parts by weight of polycarbonate resin (Panlite L-1250) was dissolved in a solution of methylene chloride to prepare a coating liquid. The coating liquid was applied onto an aluminum-deposited polyester film substrate by the wire bar technique to form a charge transporting layer having a dry thickness of 15 μm. 50 parts by weight of the compound No. III-2 and 50 parts by weight of a polyester resin (Vylon 200) were kneaded with a mixer for 3 hours together with THF as a solvent to prepare a coating liquid, which was then applied onto the charge transporting layer by the wire bar technique to form a charge generating layer having a dry thickness of 0.5 μm. Thus, a photoconductor with a structure corresponding to that shown in FIG. 3 was produced.

Example II-3

A charge transporting layer was formed in substantially the same manner as in Example II-2 except that α-phenyl-4'-N,N-dimethylaminostilbene, which is a stilbene compound, was used to replace ABPH as a charge transporting substance. Then a charge generating layer was formed on the charge transporting layer, thus a photoconductor was produced.

EXAMPLE II-4

A charge transporting layer was formed in substantially the same manner as in Example II-2 except that tri(p-toryl)amine, which is a triphenylamine compound, was used to replace ABPH as a charge transporting substance. Then a charge generating layer was formed on the charge transporting layer, thus a photoconductor was produced.

EXAMPLE II-5

A charge transporting layer was formed in substantially the same manner as in Example II-2 except that 2,5-bis(p-diethylaminophenyl)-1,3,4-oxadiazole, which is an oxadiazole compound, was used to replace ABPH as a charge transporting substance. Then a charge generating layer was formed on the charge transporting layer, thus a photoconductor was produced.

The five photoconductors thus produce were examined with respect to surface potential $V_s$, residual potential $V_r$, and half decay exposure amount $E_{\frac{1}{2}}$ for white light in substantially the same manner a in Example I-1 to I-10. The results of the measurements are shown in Table 3.

TABLE 3

| Example | $V_s$ (volts) | $V_r$ (volts) | $E_{\frac{1}{2}}$ (lux · sec) |
|---|---|---|---|
| II-1 | 710 | 60 | 5.8 |
| II-2 | 660 | 50 | 4.2 |
| II-3 | 680 | 40 | 6.2 |
| II-4 | 620 | 80 | 5.6 |
| II-5 | 630 | 50 | 4.9 |

As can be seen in Table 3, the photoconductors of Examples II-1, II-2, II-3, II-4 and II-5 were satisfactory with respect to the half decay exposure amounts and residual potentials.

EXAMPLE II-6 100 parts by weight of each of the compounds No. III-3 to No. III-28 were kneaded with a solution of polyester resin (Vylon 200) and THF as a solvent with a mixer for 3 hours to prepare a coating liquid. The respective coating liquids were applied onto aluminum substrate to form a charge generating layer having a thickness of about 0.5 μm. Further, the coating liquid of ABPH prepared in the same manner as in Example II-2 was applied on the respective charge generating layer to form a charge transporting layer having a thickness of 15 μm, thus photoconductors were produced.

Photoconductor produced in the above-mentioned manner were examined with respect to electrophotographic characteristics thereof by using the electrostatic recording paper testing apparatus (Model SP-428) in the same manner as in Example I-11 to find respective half decay exposure amounts $E_{\frac{1}{2}}$. The results of measurements are shown in Table 4.

TABLE 4

| Compound No. | $E_{\frac{1}{2}}$ (lux · sec) | Compound No. | $E_{\frac{1}{2}}$ (lux · sec) |
|---|---|---|---|
| III-3 | 6.0 | III-16 | 6.0 |
| III-4 | 5.2 | III-17 | 6.9 |
| III-5 | 4.2 | III-18 | 6.8 |
| III-6 | 5.8 | III-19 | 4.1 |
| III-7 | 6.5 | III-20 | 5.7 |
| III-8 | 6.3 | III-21 | 5.6 |
| III-9 | 4.1 | III-22 | 6.6 |
| III-10 | 5.2 | III-23 | 5.9 |
| III-11 | 6.6 | III-24 | 6.8 |
| III-12 | 7.4 | III-25 | 5.6 |
| III-13 | 6.5 | III-26 | 5.4 |
| III-14 | 5.3 | III-27 | 6.3 |

TABLE 4-continued

| Compound No. | $E_{\frac{1}{2}}$ (lux · sec) | Compound No. | $E_{\frac{1}{2}}$ (lux · sec) |
|---|---|---|---|
| III-15 | 5.7 | III-28 | 6.4 |

As can be seen in Table 4, the photoconductors using the azulenium compounds No. III-3 to No. III-28 as a charge generating substance were satisfactory with respect to the half decay exposure amounts $E_{\frac{1}{2}}$.

EXAMPLE II-7

A photoconductor having the structure as shown in FIG. 1 and comprising a photosensitive layer having a thickness of 15 μm was produced in substantially the same manner as in Example I-1 except that the compound No. III-31 was used instead of the compound No. I-1.

EXAMPLE II-8

Further, a solution of 100 parts by weight of p-diethylaminobenzaldehyde-diphenylhydrazone (ABPH) and 100 parts by weight of polycarbonate resin (Panlite L-1250) was dissolved in a solution of methylene chloride to prepare a coating liquid. The coating liquid was applied onto an aluminum-deposited polyester film substrate by the wire bar technique to form a charge transporting layer having a dry thickness of 15 μm. 50 parts by weight of the compound No. III-32 and 50 parts by weight of a polyester resin (Vylon 200) were kneaded with a mixer for 3 hours together with THF as a solvent to prepare a coating liquid, which was then applied onto the charge transporting layer by the wire bar technique to form a charge generating layer having a dry thickness of 0.5 μm. Thus, a photoconductor with a structure corresponding to that shown in FIG. 3 was produced.

EXAMPLE II-9

A charge transporting layer was formed in substantially the same manner as in Example II-8 except that α-phenyl-4'-N,N-dimethylaminostilbene, which is a stilbene compound, was used to replace ABPH as a charge transporting substance. Then a charge generating layer was formed on the charge transporting layer, thus a photoconductor was produced.

EXAMPLE II-10

A charge transporting layer was formed in substantially the same manner as in Example II-6 except that tri(p-toryl)amine, which is a triphenylamine compound, was used to replace ABPH as a charge transporting substance. Then a charge generating layer was formed on the charge transporting layer, thus a photoconductor was produced.

EXAMPLE II-11

A charge transporting layer was formed in substantially the same manner as in Example II-8 except that 2,5-bis(p-diethylaminophenyl)-1,3,4-oxadiazole, which is an oxadiazole compound, was used to replace ABPH as a charge transporting substance. Then a charge generating layer was formed on the charge transporting layer, thus a photoconductor was produced The five photoconductors thus produce were examined with respect to surface potential $V_s$, residual potential $V_r$, and half decay exposure amount $E_{\frac{1}{2}}$ for white light in substantially the same manner as in Example I-1 to I-10. The results of the measurement are shown in Table 5.

TABLE 5

| Example | $V_s$ (volts) | $V_r$ (volts) | $E_{\frac{1}{2}}$ (lux · sec) |
|---|---|---|---|
| II-7 | 630 | 70 | 4.2 |
| II-8 | 650 | 60 | 6.2 |
| II-9 | 630 | 60 | 6.5 |
| II-10 | 600 | 80 | 6.0 |
| II-11 | 610 | 50 | 5.7 |

As can be seen in Table 5, the photoconductors of Examples II-7, II-8, II-9, II-10 and II-11 were satisfactory with respect to the half decay exposure amount and the residual potential.

EXAMPLE II-12

100 parts by weight of each of the compounds No. III-33 to No. III-60 were kneaded with a solution of polyester resin (Vylon 200) and THF as a solvent with a mixer for 3 hours to prepare a coating liquid. The respective coating liquids were applied onto aluminum substrate to form a charge generating layer having a thickness of about 0.5 μm. Further, the coating liquid of ABPH prepared in the same manner as in Example II-8 was applied on the respective charge generating layer, thus photoconductors were produced.

Photoconductors produced in the above-mentioned manner were examined with respect to electrophotographic characteristic thereof by using the electrostatic recording paper testing apparatus (Model SP-428) in the same manner in Example I-11 to find respective half decay exposure amounts $E_{\frac{1}{2}}$. The results of the measurements are shown in Table 6.

TABLE 6

| Compound No. | $E_{\frac{1}{2}}$ (lux · sec) | Compound No. | $E_{\frac{1}{2}}$ (lux · sec) |
|---|---|---|---|
| III-33 | 5.8 | III-47 | 5.9 |
| III-34 | 5.0 | III-48 | 5.8 |
| III-35 | 6.6 | III-49 | 4.9 |
| III-36 | 4.1 | III-50 | 5.1 |
| III-37 | 5.9 | III-51 | 6.4 |
| III-38 | 6.5 | III-52 | 6.3 |
| III-39 | 6.1 | III-53 | 6.9 |
| III-40 | 6.3 | III-54 | 4.8 |
| III-41 | 6.9 | III-55 | 6.6 |
| III-42 | 7.8 | III-56 | 5.7 |
| III-43 | 7.1 | III-57 | 6.6 |
| III-44 | 6.3 | III-58 | 6.0 |
| III-45 | 6.4 | III-59 | 5.2 |
| III-46 | 6.2 | III-60 | 5.0 |

As can be seen in Table 6, the azulenium compounds No. III-33 to No. III-60 as a charge generating substance were satisfactory with respect to the half decay exposure amounts $E_{\frac{1}{2}}$.

According to the present invention, since an azulenium compound is used in a photosensitive layer formed on an electroconductive substrate as a charge generating substance, a photoconductor shows a high sensitivity and excellent characteristics in repeated use when adapted to either a positive charge mode or a negative charge mode.

If necessary, a covering layer may be provided on the surface of a photoconductor to improve the durability thereof.

What is claimed is:

1. A photoconductor for electrophotography, comprising:

an electroconductive substrate; and
a photosensitive layer formed on said electroconductive substrate and including a charge generating substance and a charge transporting substance, said charge generating substance comprising at least one azulenium compound represented by one of general formula (I) and (II):

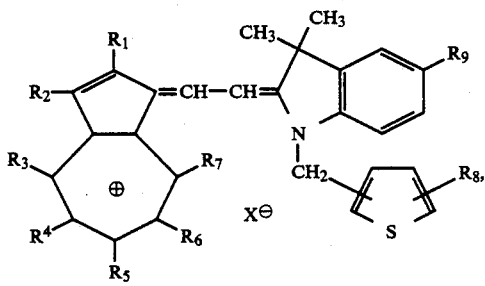

wherein each of $R_1$ and $R_9$ is selected from the group consisting of a hydrogen atom, a halogen atom, an alkoxy group, a substituted or unsubstituted alkyl group, and a substituted or unsubstituted aryl group, and $X^\ominus$ is an anion;

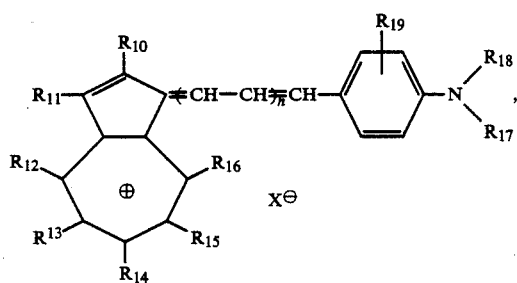

wherein each of $R_{10}$ to $R_{16}$ and $R_{19}$ is selected from the group consisting of a hydrogen atom, a halogen atom, an alkoxy group, and an aklyl group which may have a substituent(s), each of $R_{17}$ and $R_{18}$ is selected from the group consisting of an alkyl group, an aryl group, an alkenyl group, and an aralkyl group, each of which groups may have a substituent(s), and at least one of $R_{17}$ and $R_{18}$ is a thenyl group which may have a substituent(s), n is an integer and has a value of 0 or 1, and $X^\ominus$ is an anion.

2. The photoconductor as claimed in claim 1, wherein said photosensitive layer comprises a layer including a dispesion of a charge generating substance selected from azulenium compounds represented by the general formula (I) or (II) and a charge transporting substance.

3. The photoconductor as claimed in claim 1, wherein said photosensitive layer comprises a laminate of a charge transporting layer, mainly composed of a charge transporting substance, and a charge generating layer including a compound selected from azulenium compounds represented by the general formula (I) or (II).

4. A photoconductor for electrophotography, comprising:
an electroconductive substrate; and
a photosensitive layer formed on said electroconductive substrate and including a charge generating substance and a charge transporting substance, said charge generating substance comprising at least one azulenium compound represented by general formula (III):

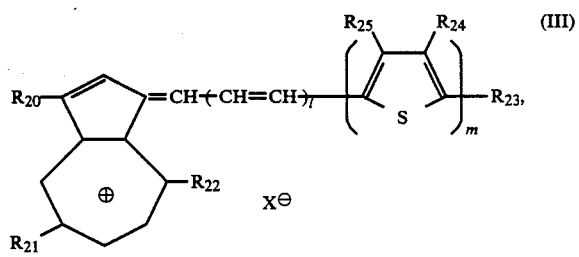

wherein each of $R_{20}$, $R_{21}$ and $R_{22}$ is selected from the group consisting of a hydrogen atom, a halogen atom, and an alkyl group, each of $R_{23}$, $R_{24}$ and $R_{25}$ is selected from the group consisting of a hydrogen atom, a halogen atom, an alkyl group, an alkoxy group, a substituted or unsubstituted aryl group, and a substituted or unsubstituted amino group, l is an integer and has a value of 0 or 1, m is an integer and has a value ranging from 1 to 5, and $X^\ominus$ is an anion.

5. The photoconductor as claimed in claim 4, wherein said photosensitive layer comprises a layer including a dispesion of a charge generating substance selected from azulenium compounds represented by the general formula (III) and a charge transporting substance.

6. The photoconductor as claimed in claim 4, wherein said photosensitive layer comprises a laminate of a charge transporting layer mainly composed of a charge transporting compound selected from azulenium compounds represented by the general formula (III).

7. A photoconductor for electrophotography, comprising:
an electroconductive substrate; and
a photosensitive layer formed on said electroconductive substrate and including a charge generating substance and a charge transporting substance, said charge generating substance comprising at least one azulenium compound represented by general formula (IV):

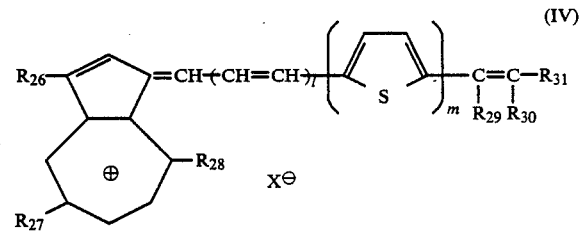

wherein each of $R_{26}$, $R_{27}$, $R_{28}$, $R_{29}$ and $R_{30}$ is selected from the group consisting of a hydrogen atom, a halogen atom, an alkyl group and an aryl group, $R_{31}$ is one of the formulae:

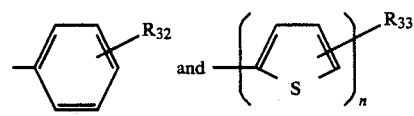

l is an integer and has a value of 0 or 1, m is an integer and has a value of 1 or 2, $X^\ominus$ is an anion, and in the structural formula of $R_{31}$, each of $R_{32}$ and $R_{33}$ is selected from the group consisting of a hydrogen atom, a halogen atom, an alkyl group, a substituted or unsubstituted aryl group, and a substituted or unsubstituted amino group, and n is an integer and has a value of 1 or 2.

8. The photoconductor as claimed in claim 7, wherein said photosensitive layer comprises a layer including a dispersion of a charge generating substance selected from azulenium compounds represented by the general formula (IV) and a charge transporting substance.

9. The photoconductor as claimed in claim 7, wherein said photosensitive layer comprises a laminate of a charge substance and a charger generating layer including a compound selected from azulenium compounds represented by the general formula (IV).

* * * * *